United States Patent [19]

Morse

[11] Patent Number: 5,166,968
[45] Date of Patent: Nov. 24, 1992

[54] PORTABLE X-RAY CASSETTE HOLDER

[76] Inventor: Arnold W. Morse, 1358 Dunhill Dr., Longwood, Fla. 32750

[21] Appl. No.: 831,490

[22] Filed: Feb. 5, 1992

[51] Int. Cl.$^5$ ............................................. G03B 42/02
[52] U.S. Cl. ................................. 378/177; 378/178; 378/180
[58] Field of Search ............... 378/177, 178, 179, 180, 378/181

[56] References Cited

U.S. PATENT DOCUMENTS

| | | | |
|---|---|---|---|
| 3,633,028 | 1/1972 | Marino | 378/180 |
| 4,045,678 | 8/1977 | Puckard | 378/180 |
| 4,352,197 | 9/1982 | Waerve | 378/177 |

*Primary Examiner*—Craig E. Church
*Attorney, Agent, or Firm*—William M. Hobby, III

[57] ABSTRACT

A portable x-ray cassette holder apparatus includes a flat radiolucent patient supporting surface having a flat base surface and a patient supporting surface. The flat base surface is spaced a predetermined spaced distance from the patient supporting surface with spacer members. An x-ray cassette holding portion holds an x-ray cassette between the patient supporting surface and the flat base for holding the cassette loaded with film in predetermined position. An x-ray cassette guide utilizes the spacing members for guiding the x-ray cassette into the x-ray cassette holder where the x-ray cassette is held in position during the taking of an x-ray. A patient gripping member handle is removably attached to the patient supporting surface in a predetermined position and extending substantially perpendicular therefrom for gripping by a patient during the taking of an x-ray in a sitting position. The flat base surface is larger than and extends out from the spaced patient supporting surface and has the handles formed therein for toting the portable x-ray cassette holder. A padded cover is removably attached with VELCRO fasteners or the like to the patient support surface and has a detachable cylindrical head support. The spacing members are cylindrical members made of a self-lubricating polymer having a bore therethrough for attaching fasteners through the spacing members to attach the patient supporting surface to the base surface and at the same time provide guides for the insertion of the x-ray cassette.

19 Claims, 2 Drawing Sheets

PORTABLE X-RAY CASSETTE HOLDER

BACKGROUND OF THE INVENTION

The present invention relates to a portable x-ray cassette holder and especially to a simplified x-ray cassette holder for taking x-rays of a patient on site.

In the past, there have been a large number of x-ray cassette holders of different types for use in connection with taking x-rays. Most of the prior art x-ray cassette holding devices are made for use in hospitals or other medical facility and are used to position the x-ray cassette holding the x-ray film which cassette is a radiolucent container which can be inserted into a holder to hold the film in place during the making of an x-ray exposure of a patient.

The present invention relates to a portable and comfortable bed top x-ray table cassette holder or film holder for the purposes of making x-ray exams and specifically for making on-site x-ray exams, such as with geriatrics patients in either a supine or vertical position. In the supine position, the present cassette holder is placed between the bed ridden patient and a bed mattress, which can be a firm or soft mattress or even a water floatation mattress, for the purpose of taking radiographs of the patient. When used in a vertical position, the patient is placed sitting on the edge of a bed, table, or other surface alongside the x-ray cassette holder and lateral chest radiography is accomplished. With the increase in medical technology, a larger proportion of the citizens tend to live longer lives and, as a result, there is a dramatic increase in the numbers who require convalescent care and with the improvement of the convalescent care, it is desirable to have these facilities as comfortable as possible for the patients during diagnostic procedures. One major difference between a typical patient in a medical facility and a convalescent patient is the agility of their bodies, with many of the older patients having osteoporosis and extremely delicate bone structure or have thin skin with little subcutaneous fat to cushion their bodies who may have decubitus ulcers or bed sores. Typically, mobile radiographic techniques are used to diagnose various conditions in convalescent patients. The convalescent radiography is performed on site at retirement homes and the like. Patients with osteoporosis, muscle atrophy, joint stiffness, and immobility are typically difficult to place an x-ray cassette under for taking the x-rays necessary for diagnostic purposes. Care must be used to avoid fractures of the vertebrae, tearing of the annular intervertebral, disc fibers, and avulsion of ligamentation and muscle fiber attachments.

There are several prior art cart top cassette holders which have not been found to be very practical in common usage because they cannot be loaded when placed upon a soft mattress and cannot be loaded from the side and slid to a desired position. None of these prior art carts were available with a level to correct beam angulation associated with table tilt on a soft mattress or water floatation and none of the prior models are small enough to be carried by hand or hanging from a portable x-ray unit. These prior art carts do not allow the patient to be easily and gently rolled onto the cassette holder at bed top and are not devised for the adherence of a friction-free skin pad to provide a comfortable cushion for the patient and the patient's head.

On site chest x-rays are routinely performed with portable units in convalescent centers and at bedside. Standard portable chest x-rays consist of an anterior to posterior view but it is desirable to also have this view accompanied with a lateral or side view. Typically, technicians sit patients up on a bedside, stack up pillows, and support the cassette with the pillows. The present invention, on the otherhand, provides a means for lateral chest radiography which is portable and in which the x-ray cassette and film are held in place at the correct level and with the patient holding the device during the exposure. The present invention also increases the patient's comfort and reduces patient motion on film and thus reduces the repeat rates and costs of taking the x-rays.

Prior art U.S. patents relating to x-ray film holders and the like can be seen in the Ruiz patent, U.S. Pat. No. 4,589,124, for an x-ray film holder for patients in a wheelchair and allows the cassettes to be attached or clamped to the wheelchair and in the Hayton, et al. patent, U.S. Pat. No. 4,651,364, for an x-ray cassette holder for a trauma stretcher. The Friedman patent, U.S. Pat. No. 2,569,561, shows a combined film holder and drain pan for radiographic examinations while the Barr et al. patent, U.S. Pat. No. 4,947,418, shows another emergency trauma board which holds an x-ray cassette for emergency x-rays. The Cook, III patent, U.S. Pat. No. 4,893,323, is a combined portable x-ray table and stretcher which allows the placement of x-ray cassettes in different positions while immobilizing the patient. The Trott patent, U.S. Pat. No. 3,774,045, teaches a cart for x-ray cassette holder which allows the x-ray cassette holders to be placed in a plurality of different positions. The Filips et al. patent, U.S. Pat. No. 4,665,574, teaches a mattress having a built-in x-ray cassette holder. The Weatherholt patent, U.S. Pat. No. 4,156,145, is an x-ray support for positioning a patient relative to a flat surface during x-ray diagnosis or radiation therapy. The Reed patent, U.S. Pat. No. 3,916,207, is a film cassette holder for facilitating the taking of x-rays of the cranium and skeletal structures and is a portable unit. The Grimm patent, U.S. Pat. No. 2,568,191, is an adjustable alignment platform for x-ray tables.

The present portable x-ray cassette holder, in contrast to the prior art, is specifically designed for taking on-site x-rays of elderly patients and the like on the patient's own bed in either a supine position or taking a lateral view without the assistance of anyone but the patient in supporting the cassette in the proper position and provides for holding the cassette as well as the alignment of the cassette for the x-ray.

SUMMARY OF THE INVENTION

A portable x-ray cassette holder apparatus includes a flat radiolucent patient supporting surface having a flat base surface and a patient supporting surface. The flat base surface is spaced a predetermined spaced distance from the patient supporting surface with spacer members. An x-ray cassette holding portion holds an x-ray cassette between the patient supporting surface and the flat base for holding the cassette loaded with film in a predetermined position. An x-ray cassette guide utilizes the spacing members for guiding the x-ray cassette into the x-ray cassette holder where the x-ray cassette is held in position during the taking of an x-ray. The patient gripping member or handle is removably attached to the patient supporting surface in a predetermined position and extends substantially perpendicular therefrom for gripping by a patient during the taking of an x-ray in a sitting position. The flat base surface is larger than and extends out from the spaced patient supporting surface and has the handles formed therein for toting the portable x-ray cassette holder. In addition, a padded cover is removably attached with VELCRO fasteners or the like to the patient support surface and has a detachable head support. The spacing members are cylindrical members made of a self-lubricating polymer having a bore therethrough for attaching fasteners through the spacing members to attach the patient supporting surface and base surface together and at the same time provide solid lubricant guides for the insertion of the x-ray cassette. A plurality of restraint openings are formed in the flat base surface portion. The base surface extends out from beneath the patient supporting surface. The x-ray cassette can be inserted from the end of the portable x-ray cassette holder either side of the rectangular x-ray cassette or either side through a larger opening for the larger side of the rectangular x-ray cassette holder.

BRIEF DESCRIPTION OF THE DRAWINGS

Other objects, features, and advantages of the present invention will be apparent from the written description and the drawings in which.

DESCRIPTION OF THE PREFERRED EMBODIMENT

Figure 1:
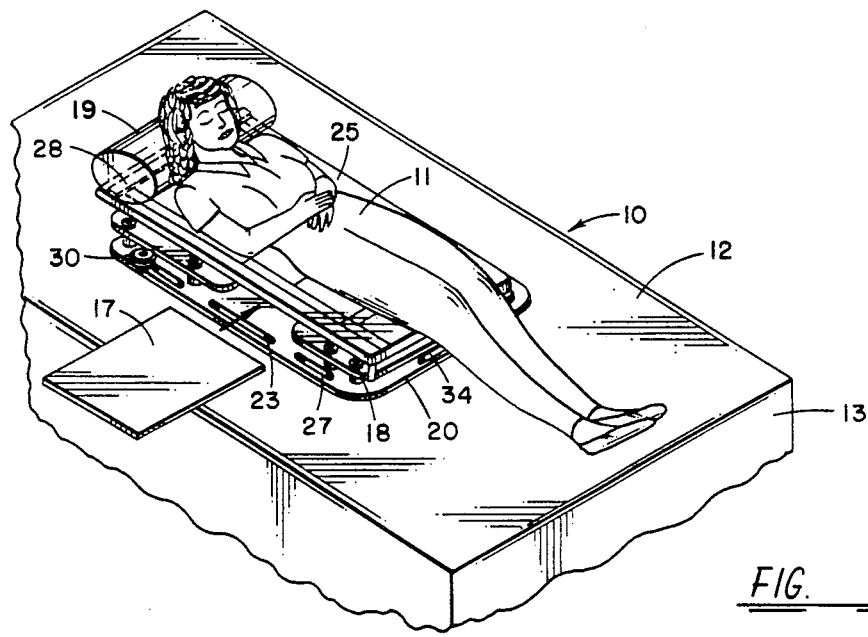
FIG. 1 is a perspective view of a portable x-ray cassette holder in accordance with the present invention placed on a bed with a patient supported thereon in a supine position.
Figure 2:
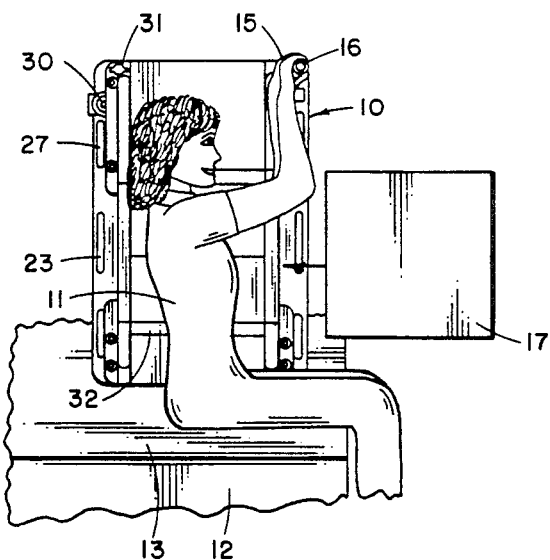
FIG. 2 is a side elevation of a portable x-ray cassette holder being held by a patient in a lateral position.
Figure 3:
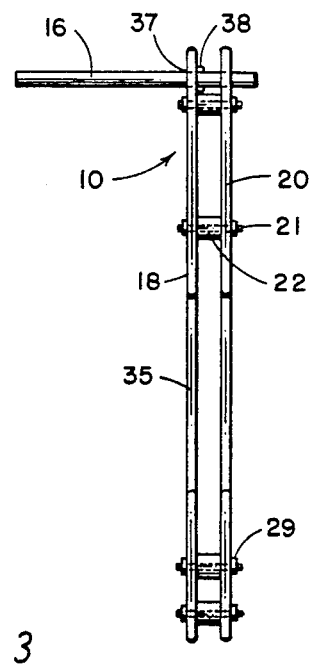
FIG. 3 is a side elevation of the x-ray cassette holders of FIGS. 1 and 2.
Figures 4, 5:
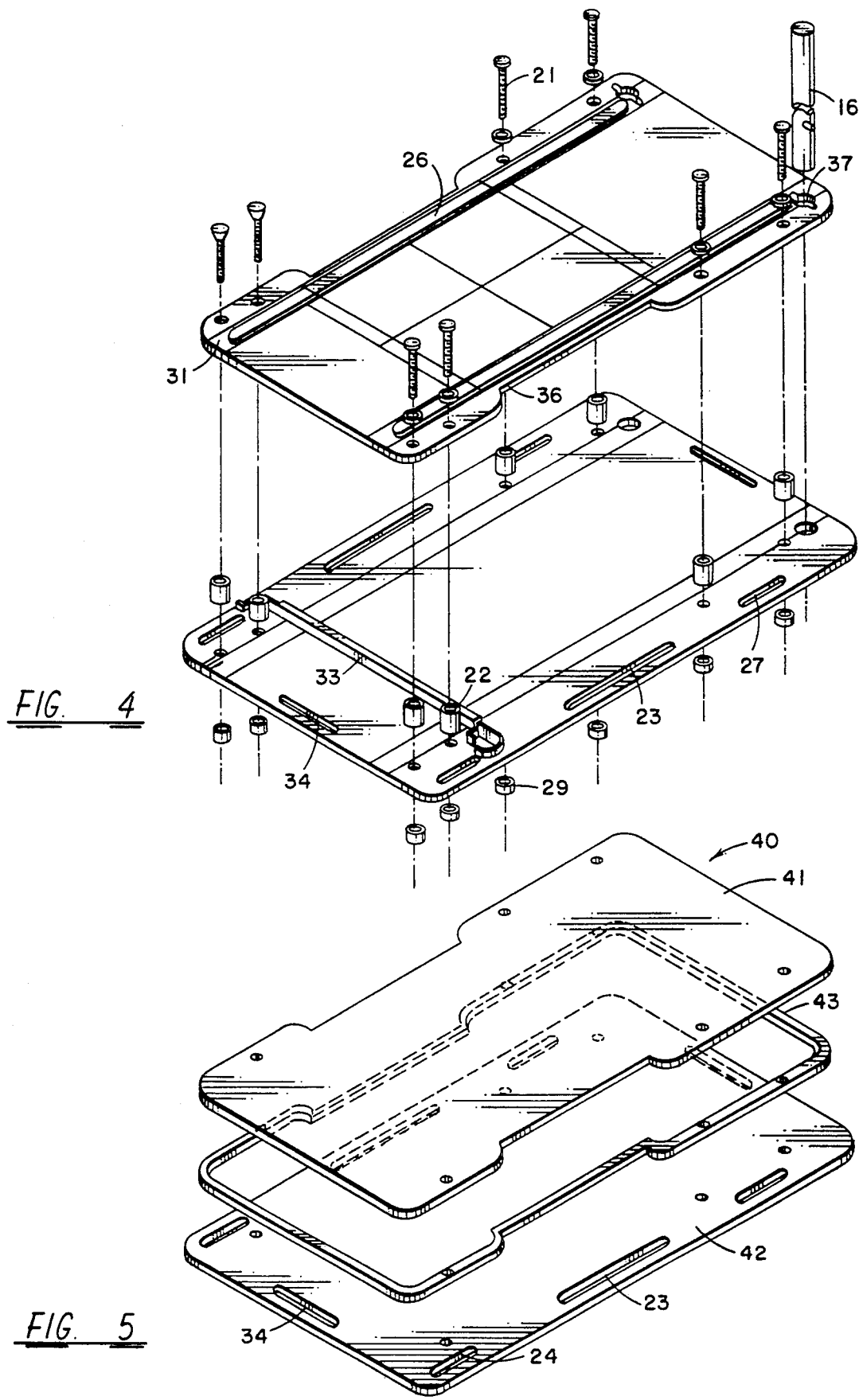
FIG. 4 is an exploded perspective view of the x-ray cassette holders of FIGS. 1–3.
FIG. 5 is an exploded perspective view of an alternate embodiment of a portion of the x-ray cassette holder in accordance with the present invention.

Referring to the drawings and especially to FIGS. 1 and 2, a portable x-ray cassette holder 10 is shown with a patient 11 in a supine position thereon in FIG. 1 with the x-ray cassette holder 10 on the patient's bed 12 and in FIG. 2 with the patient sitting upright on the mattress 13 of the bed 12 and holding the portable cassette holder 10 for a lateral x-ray. The patient is holding the cassette holder with the arms 14 and hands 15 holding an extending handle 16 which is removably attached to the portable x-ray cassette holder 10. An x-ray cassette and film holder 17 is being shown inserted into the x-ray cassette holder 10 in both FIGS. 1 and 2. The cassette holder as also seen in FIGS. 3 and 4 has a flat radiolucent patient supporting surface 18 and a parallel flat base surface 20 attached together with a plurality of bolts 21 having polymer spacers 22 spacing the surfaces 18 and 20 a predetermined distance from each other. The predetermined distance is determined by the thickness of the x-ray cassette 17. The spacers 22 are preferably of a self-lubricating polymer, such as Nylon or Teflon, and also act as guide members for directing the cassette 17 into the cassette holder in a predetermined position for taking the x-ray, shown in FIGS. 1 and 2. In addition, horizontal lines are engraved in the bottom polymer surface 20 to aide in cassette placement. The flat base surface 20 can be seen in FIGS. 1 and 4 as having a larger surface and protruding out from the bottom of the patient supporting surface 18 and having handles 23 cut in both sides thereof for grasping and supporting the portable x-ray cassette holder when moving from position-to-position. The base also has a plurality of restraint slots 24 formed in the base on areas that protrude from under the patient supporting surface 18. The patient supporting surface is ideally a radiolucent material, which can be of a plywood but can also be of an acrylic polymer or the like, when the spacing frame between the surfaces is sufficiently rigid to allow for the polymer surface to support a patient.

The x-ray cassette holder has a pad 25 mounted on top thereof with VELCRO strips 26 and has a detachable support for the patient's head. Thus, the pad 25 can be attached and readily removed by disconnecting the VELCRO strips as desired. Other fasteners, such as snap fasteners, can also be used without departing from the spirit and scope of the invention. The base unit 20 can be seen having a bullseye bubble level 30 attached thereto, in FIG. 1, which is used in FIG. 1 to level the cassette holder 10 relative to the patient 11. In FIG. 2, the pad has been removed and the lines 31 and 32 on the surface of the patient supporting surface 18 shows the operator the precise location of the film cassette 17 relative to the patient 11 so that proper views can be taken without wasted exposures. The handle 16 is attached to the cassette holder and held by the patient to hold the cassette holder in the precise vertical position, as shown in FIG. 2. This allows patient cooperation in taking the lateral x-ray without requiring an aide to hold the cassette holder in position.

Referring to FIG. 3, it can be seen that the handle 16 protrudes through an opening 37 in the panel 18 and also protrudes through an opening in the panel 22 and can be held in place with a friction grommet or washer 38 so that the handle 16 can be rapidly put in place and removed when moving from the supine position, as shown in FIG. 1 to the lateral positioning as shown in FIG. 2. Patient supporting surface 18 has identical edges 35.

As seen in FIG. 4, the plurality of bolts 21 are attached with nuts 29 with the bolts extending through the polymer spacers 22. In addition, a pair of end handles 34 are provided in the base panel 20 so that the portable unit can be supported from either end or either side for toting the unit into a facility for placing on the patient's bed. A cassette holding bar 33 is attached between a pair of spacers 22 to provide a bottom support for the cassette 17. The support 33 may be of a U-shape channel shaped for the end of the cassette to fit into so that the cassette can be slid from the side, as shown in FIG. 2. The holder 33 holds the cassette in position between the surfaces 18 and 20 and aligned for the lines 31 and 32 so that the operator can tell exactly where the film cassette is located for aiming the x-ray gun for taking the x-ray.

Turning now to FIG. 5, an alternate embodiment of an x-ray cassette holder 40 has a patient supporting or top surface 41, a base supporting surface 42, and a shaped metal frame 43 spacing the surface 41 from the surface 42. The use of a metal spacing frame of this type, in addition to guides and spacers 22, increases the rigidity of the unit and the supports so that the support surface 41 can be made of a radiolucent polymer material, such as an acrylic polymer, which will then be strong enough and rigid enough to support a patient thereon. The frame would still have a base member with handles 23 and 34 formed therein and a plurality of stiffening members 24 along with a level 30 and would still guide the film cassette with the spacers and guide members 22 (FIGS. 3 and 4).

It should be clear at this point that a portable in-bed x-ray system has been provided which can easily be carried by an operator or x-ray technician into a retirement home or care facility and rapidly set up on a patient's bed for the rapid taking of x-rays of the patient with minimal discomfort to the patient. However, it should also be clear that the present invention is not intended to be limited to the forms shown which are to be considered illustrative rather than restrictive.

I claim:

1. A portable X-ray cassette holder comprising:
   a flat radiolucent patient supporting surface;
   a flat base surface;
   spacing means attaching said flat radiolucent patient supporting surface a predetermined spaced distance from said flat base surface;
   an x-ray cassette holding means located between said patient support surface and said flat base for holding an x-ray cassette in a predetermined position;
   x-ray cassette guide means for guiding an x-ray cassette being inserted into said x-ray cassette holder into said x-ray cassette holding means between said flat patient supporting surface and said flat base surface;
   a patient gripping member removably attached to said patient supporting surface in a predetermined position and extending substantially perpendicular thereto for gripping by a patient while taking an x-ray in a sitting position; and
   handle means in the base member for transporting said x-ray cassette holder; whereby a portable x-ray cassette holder can be placed on a bed or other surface for positioning an x-ray cassette beneath or beside a patient.

2. A portable X-ray cassette holder in accordance with claim 1 in which said flat base surface is larger than patient support surface.

3. A portable X-ray cassette holder in accordance with claim 2 in which said handle is cut through flat base surface where said base surface extends beyond the patient support surface.

4. A portable X-ray cassette holder in accordance with claim 3 in which a padded cover is removably attached to said patient support surface.

5. A portable X-ray cassette holder in accordance with claim 4 in which said padded cover is a pad having a detachable cylindrical head pillow.

6. A portable X-ray cassette holder in accordance with claim 5 in which said spacing members are cylindrical members having a center bore and are attached between said patient support surface and said base surface with fasteners extending through each member bore.

7. A portable X-ray cassette holder in accordance with claim 6 in which said flat base surface has a solid lubricant polymer on one surface thereof for said x-ray cassette to slide into said cassette holder.

8. A portable X-ray cassette holder in accordance with claim 7 in which a cassette support member is attached between to two spacing members.

9. A portable X-ray cassette holder in accordance with claim 1 in which a spacing frame is shaped to follow the contour of said patient support surface and is attached thereto.

10. A portable X-ray cassette holder in accordance with claim 8 in which said gripping means is a cylindrical post attached through an opening in said patient support surface.

11. A portable X-ray cassette holder in accordance with claim 10 in which said flat base surface has a plurality of handles formed therein.

12. A portable X-ray cassette holder in accordance with claim 11 including a plurality of restraint opening formed in said flat base surface.

13. A portable X-ray cassette holder in accordance with claim 12 including a plurality of alignment lines located on said patient support surface.

14. A portable X-ray cassette holder in accordance with claim 13 including pad attaching means for supporting said padded cover onto said patient support surface.

15. A portable X-ray cassette holder in accordance with claim 14 in which said pad attaching means includes VELCRO fasteners attached to said patient support surface.

16. A portable X-ray cassette holder in accordance with claim 15 in which leveling means are attached to said flat base surface for leveling said portable x-ray cassette holder.

17. A portable X-ray cassette holder in accordance with claim 9 in which said patient support surface is a polymer surface supported with a steel frame to said base surface.

18. A portable X-ray cassette holder in accordance with claim 16 in which x-ray guide means includes cylindrical guide lines engraved into said flat patient supporting surface for guiding an x-ray cassette from either of two sides of said x-ray cassette holder.

19. A portable X-ray cassette holder in accordance with claim 18 in which said spacers are self-lubricating polymer cylinders each having a bore therethrough.

* * * * *